United States Patent
Spivey et al.

[11] Patent Number: 5,357,964
[45] Date of Patent: Oct. 25, 1994

[54] DOPPLER IMAGING DEVICE

[76] Inventors: Brett A. Spivey, 131 Seeman; Peter J. Martin, 1819 Avenida Mimosa, both of Encinitas, Calif. 92024; Douglas A. Palmer, 1229 Triesta Dr., San Diego, Calif. 92107; Todd K. Barrett, 3969 Mahaila Ave. #403, San Diego, Calif. 92122

[21] Appl. No.: 14,856

[22] Filed: Feb. 8, 1993

[51] Int. Cl.$^5$ .............................. A61B 8/06
[52] U.S. Cl. ............................... 128/661.09
[58] Field of Search ......... 128/661.03, 661.07–661.10; 73/602, 861.25; 364/413.25

[56] References Cited

U.S. PATENT DOCUMENTS

| | | | |
|---|---|---|---|
| 4,542,657 | 9/1985 | Barber et al. | 128/661.09 X |
| 4,693,319 | 9/1987 | Amemiya | 128/661.02 |
| 4,803,990 | 2/1989 | Bonnefous et al. | 128/661.08 |
| 4,979,513 | 12/1990 | Sakai et al. | 128/661.09 |
| 5,072,734 | 12/1991 | Takeuchi | 128/661.09 X |
| 5,081,993 | 1/1992 | Kitney et al. | 128/661.08 |
| 5,111,823 | 5/1992 | Cohen | 128/660.07 |
| 5,201,313 | 4/1993 | Katakura | 128/661.09 |
| 5,213,105 | 5/1993 | Gratton et al. | 128/664 |
| 5,224,482 | 7/1993 | Nikoonahad et al. | 128/661.08 |
| 5,230,340 | 7/1993 | Rhyne | 128/661.01 |
| 5,291,892 | 3/1994 | O'Donnell | 128/661.08 |

*Primary Examiner*—Francis Jaworski
*Attorney, Agent, or Firm*—John R. Ross

[57] ABSTRACT

A device and method for producing an image of a fluid moving through a medium. An acoustic wave insonifies the medium to produce Doppler shifted scattering from randomly located scatterers in the moving fluid. At least eight channels of acoustic detectors detect signals reflected from the medium and the amplitudes of the scattered signal is determined at each channel for at least one Doppler shifted frequency. Time averaged channel-to-channel amplitude correlations are produced using the Doppler shifted amplitude data from which the image of the moving fluid is calculated.

29 Claims, 11 Drawing Sheets

DOPPLER IMAGING DEVICE

BACKGROUND OF THE INVENTION

This application in part discloses and claims subject matter disclosed in our earlier filed pending application Ser. No. 07/891851, filed Jun. 1, 1992. This invention relates to acoustic imaging device, and more particularly, to Doppler imaging devices.

The prior art of Doppler detection and imaging techniques has advanced mainly in three areas: continuous wave Doppler detection, pulsed-Doppler detection, and color-flow Doppler imaging.

Continuous-Wave Doppler

Continuous-wave Doppler systems continuously transmit ultrasound into human tissue. Echoes arise in the tissue and return to the receiving transducer. Dominating the return echoes are very strong signals from stationary sources. Superimposed on the strong signals are smaller Doppler shifted waves arising from moving tissue components.

CW Doppler systems normally use a single split element transducer, which continuously transmits and receives ultrasound. One transducer element transmits the carrier frequency into the tissue and the other receiving element amplifies the return signals, which are compared to the carrier signal to produce the Doppler signal. The Doppler signal then goes to a spectral analyzer which outputs the Doppler frequencies.

CW Doppler is used in medicine for monitoring blood flow velocities. The CW Doppler system obtains information along a line extending from the transducer. Thus, it does not produce an image of moving blood because of the lack of range information.

Pulsed Doppler Imaging

Pulsed Doppler imaging is a well known technique commonly used in ultrasonic medical applications. A transducer transmits a tone burst of acoustic energy into a medium and from the backscattered pulse interrogates the Doppler shift by mixing with the transmitted pulse. Range-gating, beam focusing and beam steering allow collection of Doppler information at a specific volume element inside the tissue. The resolution is the size of the volume element which is laterally determined by the focused beam waist and axially determined by range gating. Pulsed-Doppler tracks the phase of the received signal at the pulse repetition frequency (5–20 kHz), thus yielding a time series of the Doppler shift at a specific point.

Color Flow Doppler Imaging

Color Flow Doppler is pulsed Doppler displayed on multiple points to form an image. A linear phased array of transducers forms dynamically focused beams that scan the array. The image is separated into sampling sites approximately one acoustic wavelength long. The phase information is used to indicate motion, and based on phase changes the system separates an echo signal into forward and reverse channels, which depict the presence and direction of motion as colors.

A time-domain correlation method is also used to form an image of the velocity of moving blood. This method correlates in time successive pulse-echo scan lines to obtain an image of the velocity of moving blood. The direction and velocity of the moving blood is again depicted as colors.

Both color-flow Doppler imaging and time domain correlation imaging form the image first with a beamformer, and then look for changes in that image by using a Fourier transform or correlation technique.

SUMMARY OF THE INVENTION

The present invention provides a device and method for producing an image of a fluid moving through a medium. An acoustic wave insonifies the medium to produce Doppler shifted scattering from randomly located scatterers moving in the medium. At least eight channels of acoustic detectors detect signals reflected from the medium and the amplitude of the scattered signal is determined at each channel for at least one Doppler shifted frequency. Time-averaged receiver channel-to-channel amplitude correlations are produced using the Doppler shifted amplitude data from which the image of the moving fluid is calculated.

The invention disclosed in this patent application differs from the prior techniques in the following ways:

1. We form amplitude correlations between individual receiver channels.
2. We form these correlations without first using a beamformer to form an image.
3. We form an image from the receiver channel-to-channel amplitude correlations with algorithms not used in the prior techniques.

DETAILED DESCRIPTION OF PREFERRED EMBODIMENTS

The Concept

Figure 1:
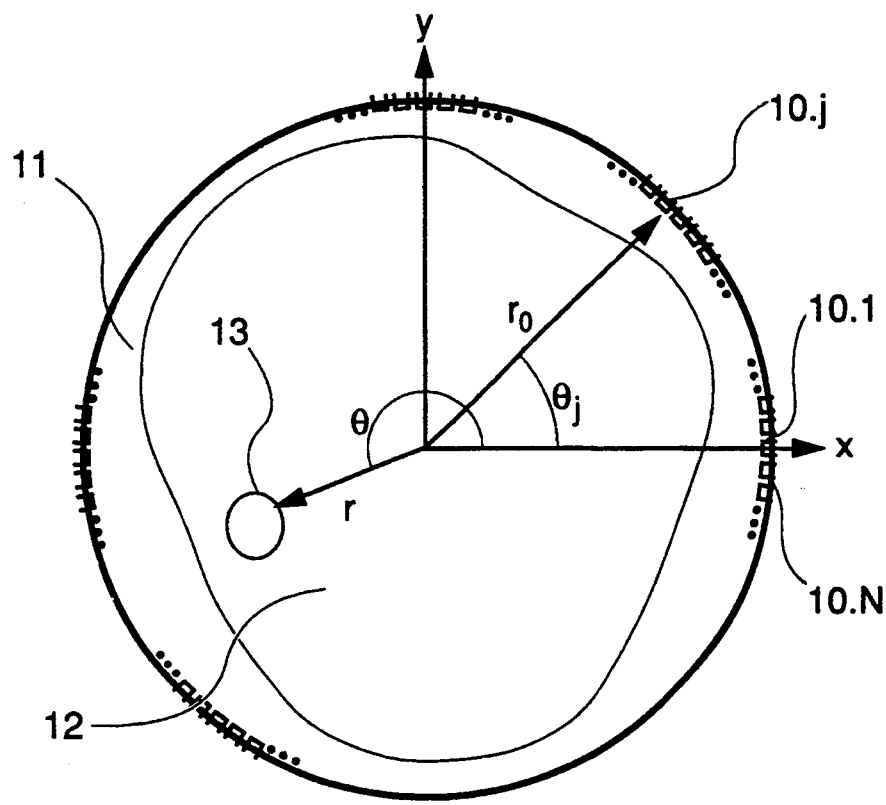
FIG. 1 is an illustration of the system of acoustic transducers utilized in this invention.

One preferred embodiment of the present invention provides a system for insonifying a medium with a single frequency acoustic wave from a single direction, a system for measuring the amplitude and phase of acoustic waves scattered into a plurality of directions from the medium, and an efficient mathematical algorithm for determining a two-dimensional flow velocity map from this set of acoustic wave information. A schematic diagram of the cross section of a portion of this embodiment is shown in FIG. 1.

In this embodiment, there are $N=256$ acoustic transducers $10.1, \ldots, 10.N$ arranged in the r-$\theta$ (or x-y) plane on the locus of a circular 360 degree arc of radius $r_o$. The transducers 10 act as receivers of acoustic waves. The z-direction is perpendicular to this plane. The transducers circumscribe the medium 12 which is semi-transparent to the acoustic waves. In this preferred embodiment, a fluid resides in the remaining volume 11 to effectively couple acoustic waves between the transducers 10 and the medium 12. Water is a preferred coupling fluid for imaging human tissue. When imaging other objects a fluid should be chosen which preferably has a density $\rho_o$ and sound speed $c_o$ which are approximately equal to the average density and sound speed of the medium 12.

Figure 3:
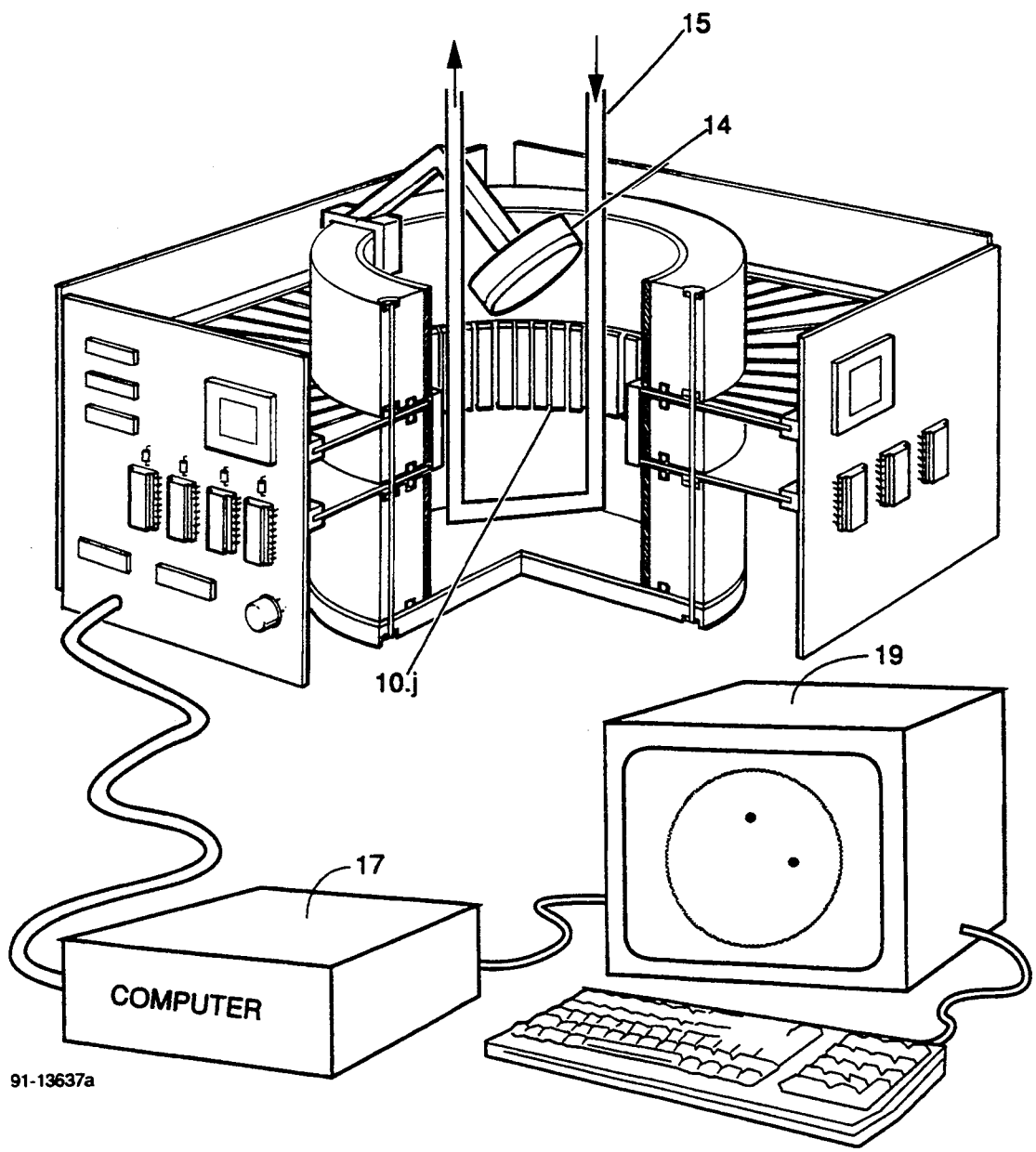
FIG. 3 is a schematic diagram of the invention used to test the concept in a water bath.

A continuous acoustic wave $p_o(t):\cos[\bar{k}\cdot\bar{r}-\omega_o t+\phi]$, where $\phi$ is a constant phase delay $$k = \frac{2\pi}{\lambda}$$

and $\omega_o = kc_o = 2\pi f_o$, where $f_o$ is typically 1 to several MHz, is transmitted from acoustic transducer 14 into human tissue as shown in FIG. 3. The tissue contains a plurality of vessels 13 which carry flowing fluid such as blood, for example. The moving blood cells scatter Doppler-shifted sound waves into all directions. The Doppler shift caused by a blood cell with velocity $\bar{v}$ is $\omega = \bar{k}\cdot\bar{v}$, corresponding to a frequency shift $$f = \frac{\omega}{2\pi} = \frac{\vec{k}\cdot\vec{v}}{2\pi}.$$

For typical blood flow, $v \leq 1$ m/sec giving $f \leq 1000$ Hz for an acoustic wavelength $\lambda = 1$ mm ($f_o = 2$ MHz) thus, the Doppler frequency $f << f_o$. The acoustic wave incident on receiver 10.j can be written $p_j(t)=m_j(t)\exp[-i\omega_o t]$, a form which separates the signal into its carrier component and the complex amplitude $m_j(t)$ containing the Doppler shift. The complex amplitude $m_j(t)$ contains a constant pan due to a combination of acoustic waves scattered from the static tissue and the time-dependent part due to Doppler-shifted acoustic waves scattered from the flowing blood.

The measured complex amplitude $m_j(t)$ at receiver 10.j can be written as:

$$m_j(t) = \int f(\bar{r},t) D_j(\bar{r}) d^2\bar{r} \qquad (1)$$

where $D_j(\bar{r})$ is the antenna pattern for receiver 10.j. The source function $f(\bar{r},t)$ is the complex amplitude for the transmitted acoustic wave to scatter from a volume element located at position $\bar{r}$. The volume element can contain static tissue (static $f(\bar{r})$) or flowing fluid (time dependent $f(\bar{r},t)$). We Fourier transform equation (1) in time to yield $$X_j(\omega) = \int F(\bar{r},\omega) D_j(\bar{r}) d^2\bar{r} \qquad (2)$$

where $F(\bar{r},\omega)$ is the Fourier transform of the source function $f(\bar{r},t)$. Next, we correlate all pairs of receivers by forming the correlation matrix $$X_j(\omega)X_k^*(\omega) = \int D_j(\bar{r})D_k^*(\bar{r}') F(\bar{r},\omega)F^*(\bar{r}',\omega) d^2\bar{r}d^2\bar{r}' \qquad (3)$$

where $<\ldots>$ denotes an ensemble average over different realizations of $X_j(\omega)$. In the case of flowing fluid, a realization of $X_j(\omega)$ consists of the acoustic Doppler spectrum from a specific collection of discrete scatterers. The algorithm relies on the fact that the scattering particles in the blood are randomly distributed in the blood vessel. Furthermore, since the particles are moving, the distribution of particles in the scattering volume varies randomly as a function of time, so a time average of the moving particles is equivalent to the ensemble average in equation 3. In the mathematical terms of random processes, the algorithm relies on the fact that the spatial part of the complex source function $f(\bar{r},t)$ consists of a sum of localized point-like scattering points (with size $<<1$), each multiplied by a random complex amplitude $\exp[i\xi]$, where $\xi$ is a Gaussian random phase. Thus, we can replace the ensemble average on the right-hand side of equation (3) with the form appropriate to random incoherent radiators:

$$F(\bar{r},\omega)F^*(\bar{r}',\omega) = \delta(\bar{r}-\bar{r}')S(\bar{r},\omega) \qquad (4)$$

In equation (4), $S(\bar{r},\omega)$ is the power radiated at $\bar{r}$ at Doppler frequency $\omega$. Inserting equation (4) into equation (3), we arrive at $$X_j(\omega)X_k^*(\omega) = \int D_j(\bar{r})S(\bar{r},\omega)D_k^*(\bar{r})d^2\bar{r} \qquad (5)$$

We will denote the ensemble average correlation matrix $$X_j(\omega)X_k^*(\omega) \equiv R_{jk}(\omega). \qquad (6)$$

Obtaining an image of the flow medium using our embodiment consists of inverting equation (5) for the source power distribution, $S(\bar{r},\omega)$.

The antenna pattern $D_j(\bar{r})$ appearing in equations (1), (2), (3), and (5) represents the response of the receiver 10.j to incident acoustic radiation. The radiation pattern of any acoustic transducer can be exactly calculated as a weighted sum of monopole, dipole, quadrupole, ... patterns, as discussed, for example, by J. D. Jackson in Chapter 16 of "Classical Electrodynamics" (John Wiley, New York, 1962). Our Doppler reconstruction algorithm can be executed with any choice of $D_j(\bar{r})$, including the experimentally measured antenna pattern. For our preferred embodiment, the transducers closely resemble dipoles in the x-y plane (see FIG. 1), so $D_j(\bar{r})$ is the solution of the Helmholtz equation with dipole source term:

$$\nabla^2 D_j(r) + k_o^2 D_j(r) = \delta'(\bar{r}-\bar{r}_o)\delta(\theta-\theta_j) \qquad (7)$$

The antenna pattern in the z-direction is collimated in our preferred embodiment.

In equation (7), $$\delta'(r - r_o) = \frac{d}{dr} \delta(r) \Big|_{r=r_o},$$

corresponding to a coherent sum of two monopole (point) receivers which straddle the boundary along the radial direction. Using $$\nabla^2 = \frac{\partial^2}{\partial r^2} + \frac{1}{r^2} \frac{\partial^2}{\partial \theta^2} \quad (10)$$

for the polar geometry of FIG. 1, the solution to equation (7) is $$D_j(r, \partial 4) = \sum_{m=-\infty}^{m} e^{im(\theta - \theta_j)} H_m'(k_o r_o) J_m(k_o r) \quad (8)$$

In equation (8), we have omitted a normalization constant which does not effect the reconstruction algorithm, since only the distribution of the data, and not the absolute magnitude, is important. The function $J_m(z)$ is the Bessel function of integer order m and $H'_m(z)$ is the first derivative of the Hankel function of order m. These functions are tabulated in Chapter 9 of "The Pocketbook of Mathematical Functions" by M. Abramowitz and I. Stegun (Verlag Ham Deutsch, 1984). In this reference one can also find Graf's identify, which allows equation (8) to be simplified to $$D_j(r,\theta) = -H_1(w) \cos \frac{1}{2} [\pi - (\theta - \theta_j)] \quad (9)$$

where $$w = k_o \sqrt{r^2 + r_o^2 - 2 r r_o \cos(\theta - \theta_j)}.$$

Equation (5) theoretically justifies our principal claim, namely that detection using the embodiment pictured in the location, $\bar{r}$, FIG. 1 provides incoherent Doppler-scattered data that suffices to characterize the source power distribution of flowing blood in tissue. We will now proceed to discuss several ways to solve equation (5) for the source function $S(\bar{r},\omega)$. $S(\bar{r},\omega)$ is power spectrum of acoustic signals scattered at a Doppler shifted frequency $\omega$ and position $\bar{r}$ and thus presents an "image" of the flowing fluid.

Reconstruction Methods

In theory, we could reconstruct, from equation (5), the source power distribution $S(\bar{r},\omega)$ as a continuous function of the Doppler shift frequency $\omega$ at each spatial point $\bar{r}$. In practice, we will reconstruct $S(\bar{r},\Delta\omega_\beta)$ for an average of frequency bands $\Delta\omega_\beta$ and finite spatial pixels $\bar{r}_\alpha$.

To discuss the inversion techniques, first we adopt a notation which allows us to write the equations of Doppler imaging in matrix-vector form. Let Greek indices ($\alpha, \beta, \ldots$) refer to coordinates $\bar{r}$ in the x-y or r-$\theta$ plane, so a function $G_j(\bar{r})$ labeled by the jth receiver coordinate and evaluated at the pixel location $\bar{r}_\alpha$ is denoted by $G_{j\alpha}$. Integrals over the coordinate $\bar{r}$ are then written as a sum over $\alpha$; for instance $$\int G_j(\bar{r}) d^2 \bar{r} \rightarrow \sum_{\alpha} G_{j\alpha}.$$

Also, we denote the average of Doppler frequency bands as $\Delta\omega_{62}$. This is depicted graphically in FIG. 5. With this notation, we can rewrite equations (2), (4), (5) and (6):

$$X_j = \sum_{\alpha} D_{j\alpha} f_\alpha + n_j \quad (10)$$

$$\langle F_\alpha F_\beta \rangle = S_\alpha \delta_{\alpha\beta} \quad (11)$$

$$\langle X_j X_k^* \rangle = \sum_{\alpha} D_{j\alpha} S_\alpha D_{\alpha k}^T + N_{ij} \quad (12)$$

In equation (10), we have added noise to each measurement $X_j$, so the covariance of the noise, $N_{ij=n_i n_j}$, now appears in equation (12). In equations (10)–(12), it is implied that the variable $\omega$ is fixed at an average of a specific frequency band $\Delta\omega_{62}$. We will reconstruct spatial maps of $S(\bar{r}_\alpha, \Delta\omega_\beta)$ for each separate frequency band $\Delta\omega_\beta$ and then combine this information to form an image.

The above equations define a class of mathematical problem called beamforming, which refers to the determination of a distribution of radiators given an ensemble of noisy field measurements along an antenna array. Equation (12) can be written in matrix form $$R = DSD^T + N. \quad (13)$$

A number of different techniques have been developed to solve this equation for passive beam forming applications, any of which could be applied to obtaining an image $S(\bar{r},\omega) = S_\alpha(\omega)$ of flowing blood from equation (13). We will briefly list some common methods, referring to the article "Multiple Emitter Location and Signal Parameter Estimation," by R. O. Schmidt (IEEE Trans. Antennas and Propagation, AP 14. p. 276, 1986) for comments on their relative merits. Then we will elaborate on one method, maximum likelihood, which we have shown to work well on real data. Finally, we will also show that a reconstruction method that we developed for coherent ultrasound tomography (see pending patent application Ser. No. 07/891,851, filed Jun. 1, 1992) can be used to obtain a Doppler image.

Ordinary beamforming performs a direct inversion of equation (13):

$$S_\alpha^{BF} = (D^T R D)_{\alpha\alpha} \quad 14)$$

where the subscript $\alpha\alpha$ denotes the diagonal term of a column of the square matrix.

Because the antenna pattern is broad, $S_\alpha^{BF}$ will show broad peaks in the direction of blood scatterers, but this method does not resolve different scatterers as required for an image. The so-called music algorithm (referenced above by Schmidt) solves equation (13) for the case of sparse radiators by separating the vector space into a signal space (spanned by the vectors $D_j$) and a noise subspace (spanned by the eigenvectors of N). The number of incident signals can be determined by computing the eigenvalues of R in the noise representation, and the image is then given by $$S_\alpha^{MU} = \frac{1}{(D^T E E^T D)_{\alpha\alpha}} \quad (15)$$

where E is the matrix whose columns are the eigenvectors of the noise matrix, N. In non-medical applications, the music algorithm has been shown to locate distinct acoustic radiators in the presence of noise. The maximum entropy estimator obtains an image for each receiver, $$S_\alpha^{ME} = \frac{1}{(D^T CC^T D)_{\alpha\alpha}} \quad (16)$$

where C is a column vector of R. It selects one of the array elements 10.j as a reference and finds weights to apply to the remaining signals to minimize the mean-square error between the reference signal and the linear estimate. The maximum likelihood estimator assumes that the measurements X in equation (13) correspond to a zero mean, multiparameter Gaussian process. Baye's theorem is used to derive an expression for the conditional probability, P(S;X), of a given source S given the measurements, X. The function P(S;X) is then maximized by minimizing the log-likelihood function, ln P(S;X), with respect to S, with the constraint Set$_\alpha$>0, for all $\alpha$. Conventional maximum likelihood uses $$S_\alpha^{ML} = \frac{1}{(D^T R^{-1} D)_{\alpha\alpha}} \quad (17)$$

to obtain an image. We have found that equation (17) produces good images using our embodiment. Improved images can be generated by including higher-order correlations through extending the maximum likelihood formalism. Minimizing ln P(S;X) results in the following non-linear equation to be solved for S:

$$D^T(N+DSD^T)^{-1}(N+DSD^T-XX^T)(N+DSD^T)^{-1}D_{\alpha\alpha}=0 \quad (18)$$

Equation (18) can be solved iteratively by assuming an initial first-order solution $XX^T = R_1 = N + DSD^T$, so that $(N+DSD^T)^{-1} \simeq R_1^{-1}$. The first-order estimate for $S_\alpha$ is then $$S_\alpha = [|D^T R_1^{-1} D|^2_{\alpha\beta}]^{-1}[D^T R_1^{-1} D_{\beta\beta} - D^T R_1^{-1} N R_1^{-1} D_{\beta\beta}]. \quad (19)$$

This solution has been shown to work well on our simulated Doppler data. An alternative iterative method follows if one uses $(N+DSD^T)^{-1} = R_1^{-1}$ only once in equation (18):

$$S_\alpha^{-1} = (D^T R^{-1} D)_{\alpha\alpha} + (S^{-1}(S^{-1}+D^T N^{-1} D)^{-1}S^{-1})_{\alpha\alpha} \quad (20)$$

Equation (20) may be iterated by using the maximum likelihood estimate equation (17) (first term on right-hand side of (20)) as a first approximation $S_1^{-1}$ to, and $S^{-1}$, and evaluating the second term on right-hand side of equation (20) using $S_1^{-1}$.

Another method of inverting equation (13) exploits the mathematical similarity to the reconstruction of coherent ultrasound tomography as described in pended patent application Ser. No. 07/891,851, filed Jun. 1, 1992. Ultrasound tomography solves for a source function S($\bar{r}$) given measurements $$M_{jk} = \int a_j(\vec{r}) S(\vec{r}) a_k(\vec{r}) d\vec{r} \quad (21)$$

where j and k are transducers 10.j. The form in equation (21) results from the fact that in coherent tomography, receivers 10.j are used one at a time as transmitters, allowing measurements (21) to be mapped out for all pairs of transmitters/receivers. In equation (21), $a_j(\bar{r})$ is the solution to the Hemholtz equation for a dipole transmitter at $\bar{r}_j$, including effects of multiple reflections. In the absence of multiple reflections, it is identical to the antenna function $D_j(\bar{r})$. Formally, equation (21) is identical to the Doppler equations (5)–(6), with $M_{jk} \rightarrow R_{jk}$, $a_j(\bar{r}) \rightarrow D_j(\bar{r})$, and $a_k(\bar{r}) \rightarrow D_k^*(\bar{r})$. Thus, the linear Fourier transform method described in the above patent application to solve equation (21) can directly applied to obtain an image from Doppler-scattered waves using our embodiment.

The frequency variable $\omega$ in the equations above corresponds to the Doppler frequency shift imparted to the signal scattered from that portion of medium 12 which is moving. The magnitude of the $\omega$ depends on the vector velocity of the medium, the vector wavenumber $\bar{k}$, and the position at which the scattered wave is measured. For the case where the scattering medium is measured in a single plane perpendicular to the velocity of the medium $\omega = \bar{V} \cdot \bar{k}$. Thus, the solution, S($\bar{r},\omega$), for equations (5) and (6) represents a statistical estimate of the expected or average number of particles at $\bar{r}$ with velocity corresponding to a Doppler frequency shift $\omega$. In principle, a velocity map of all points in the medium may be determined by calculating S($\bar{r},\omega$) for all reasonable $\omega$. In this case the following relation holds, $$V_z(\vec{r}) = C \int S(\vec{r},\omega) \frac{\lambda \omega}{2\pi \cos\theta} d\omega, \quad (22)$$

where $V_z$ is the average value of the velocity perpendicular to the plane containing the receiver transducers, C is a constant set by the configuration of the test device, and $\theta$ is the angle between the fluid velocity vector and the wavenumber vector $\bar{k}$.

A means of improving the accuracy and reliability of the estimate $V_z(\bar{r})$ can be achieved by measuring $R_{jk}(\omega)$ for more than one insonifying frequency $\omega_o$. This could be accomplished sequentially; first insonifying the medium with a single frequency $\omega_o^{(1)}$, measuring the scattered signal and storing the data, then repeating this step for as many frequencies, $\omega_o^{(i)}$, as desired. Equations (5) and (6) could then be solved for each insonifying frequency and the final result would be the obtained by averaging the individual estimates of S for frequency shifts corresponding to the same scattering particle. If the total number of insonifying frequencies used is I then the velocity may be written as follows:

$$V_z(\vec{r}) = \frac{1}{I} \sum_i^I C^{(i)} \int \frac{S^{(i)}(\vec{r},\omega) \lambda^{(i)} \omega}{\cos\theta} d\omega, \quad (23)$$

In practice, using multiple insonifying frequencies will help alleviate errors arising from the inexact knowledge of the antenna functions $D_j(\bar{r})$.

If the velocities of the scattering medium are confined to a finite range such that $\|\bar{v}_m\| << c$, where c is the soundspeed of the insonifying wavefront, and $\bar{v}_m$ is the maximum velocity present in the flow, then the Doppler shifts are relatively small compared to $\omega_o$. In this case S($\bar{r}\omega$) is narrowband, $$S(\vec{r},\omega) = 0 \text{ when } \omega < \frac{-2\pi v_m}{\lambda} \text{ or } \omega > \frac{2\pi v_m}{\lambda}, \quad (24)$$

and it is possible to transmit multiple insonifying frequencies simultaneously. The medium is insonified with a complex waveform which has power at several $\omega_o^{(i)}$ separated in frequency by more than the largest possible Doppler shift. The scattered signal may then be separated into distinct wavebands; one for each of the different insonifying frequencies. For example, if the largest velocity is $v_m=3$ m/sec, then the maximum Doppler shift is $$\frac{\omega}{2\pi} = 6 \text{ kHz}$$

at insonifying frequency $$\frac{\omega_0}{2\pi} \simeq 3 \text{ MHz}.$$

Therefore, one could simultaneously transmit a comb of frequencies, $\omega_0^{(i)}$ separated by $$\frac{\Delta\omega}{2\pi} \simeq 20 \text{ kHz}.$$

Figure 2:
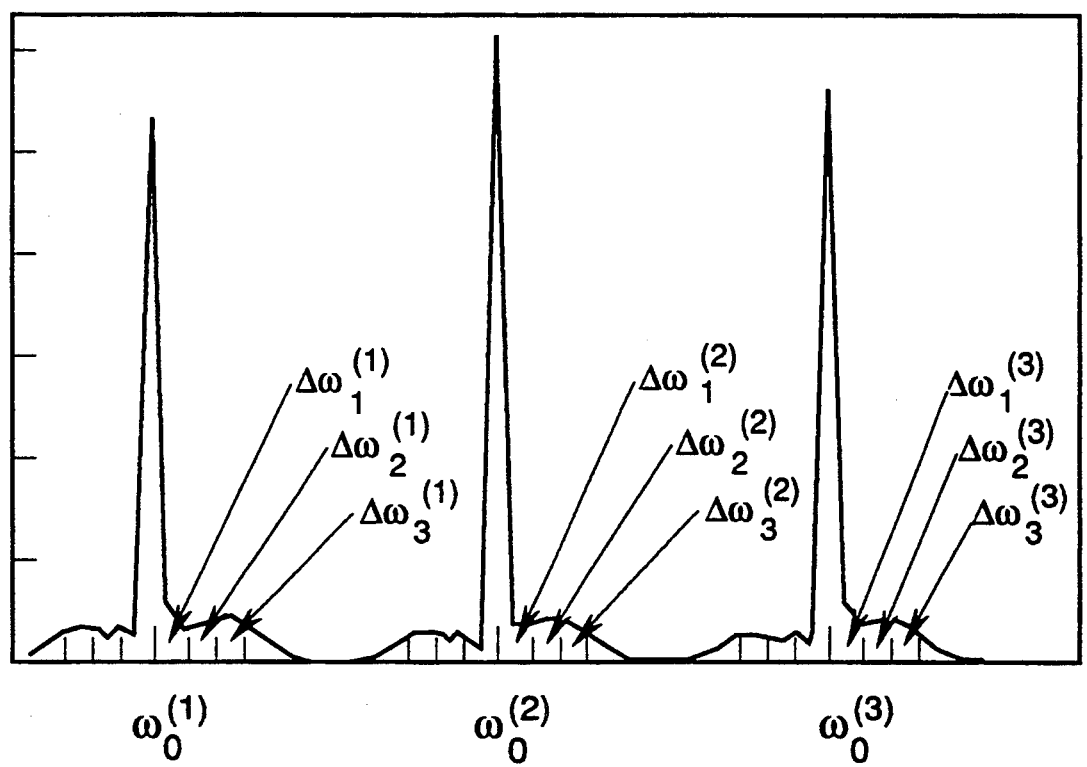
FIG. 2 is the spectrum of received Doppler information from simultaneous insonification at three discrete frequencies.

FIG. 2 illustrates this situation for an insonifying signal composed of three sine waves. The power spectrum of the scattered signal at a single transducer 10.j is shown. There is a strong spike at each insonifying frequency due to the sound scattered from the stationary part of the medium 12. The side lobes to either side of the main insonifying frequency peaks represents the Doppler shifted waves scattering from the moving portions of 12. Since the $\omega_0^{(i)}$ are separated by more than the largest Doppler shift, the side lobes around any of the main frequency peaks goes to zero before the side lobes from any of the other insonifying frequencies become non-zero. The determination of the scattering potential and fluid velocity can then be accomplished using equation (23) just as if the medium had been sequentially insonified with simple single frequency wavefronts.

The Device

A sketch of an embodiment of the device used to test the Doppler imaging concept is shown in FIG. 3. A continuous-wave 500 kHz sound wave is transmitted into a medium containing plurality of vessels which carry flowing fluid such as blood, for example. Inhomogeneities in the flowing fluid (such as red blood cells) scatter the sound wave in all directions. A separate receiver array 10 interrogates the scattered sound waves emanating from the fluid. In the present system the receiver array consists of 256 transducer elements evenly arranged on a circle. Our test set up used a water bath to couple the sound waves to a Latex tube 15 containing the moving fluid. The receiver array was connected electronically to a computer 17 for high-speed data acquisition and data processing, and an image display unit 19.

Figure 5:
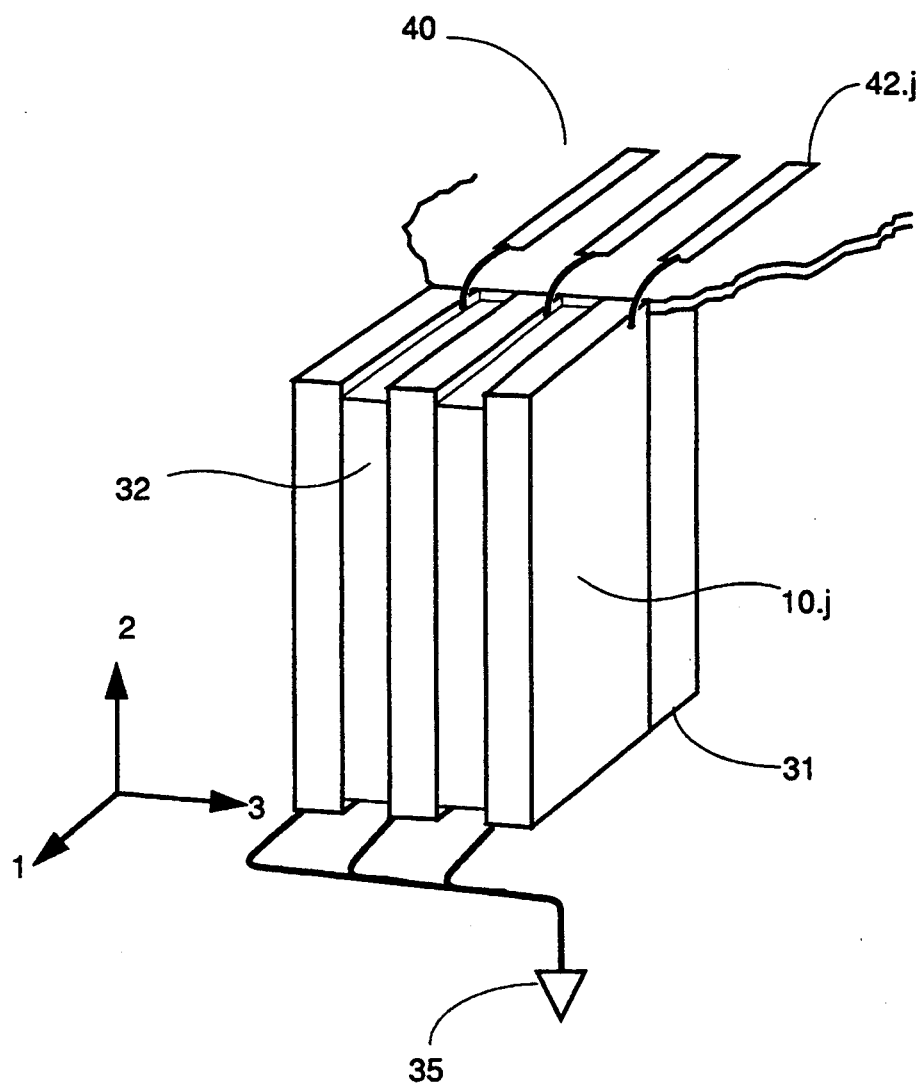
FIG. 5 is a detailed illustration of several of the acoustic transducers.

The transducer portion of the present embodiment of the invention is displayed in FIG. 5. The device consists of $N=256$ acoustic transducers 10 evenly spaced on a circle of radius $r_o=51$ mm which act as receivers, and an insonifying transducer 14. The insonifying transducer is placed above or below the receiver transducers 10, and positioned in a way to insonify the test medium with a beam of ultrasonic radiation. Each of the acoustic transducers 10 performs as a receiver of the acoustic waves scattered by inhomogeneities with in the test medium. The frequency of the insonifying waves is set at approximately 500 kHz which results in a wavelength $\lambda_o \approx 3.0$ mm in water and nearly the same wavelength in human tissue. The spacing between the receiver transducers 10 is 1.3 min. In the preferred embodiment, the acoustic antenna pattern for each transducer is fairly uniform with angle but is somewhat more sensitive in the radial (r) dimension which lends itself either to the monopole or to the dipole approximation for the steering functions $D_j$ used in the aforementioned derivation of the reconstruction algorithm. The vertical height of the transducers is 25.4 mm, which produces a fairly collimated receiver antenna pattern in the z-direction. The thickness of the image slices is roughly equal to the vertical (z) height of the transducers so the image S(x) will comprise an average over the vertical dimension. Alternate embodiments include varying the vertical height to obtain different image slice dimensions.

Each transducer element 10.j (j=1, ..., 256) is constructed from PZT5A piezoelectric ceramic supplied by Vernitron Piezoelectric Division, Bedford, Ohio. The dimensions of each element are 0.90 mm (3-axis)×2.80 mm (1-axis)×25.4 mm (2-axis). Electrical energy is supplied along the 3-axis and the 1-axis is dimensioned so that the transducer can resonantly receive acoustic energy in a range centered around 50) kHz along the 1-axis. Each transducer backing 31 and the spacing between the transducers 32 is comprised of an air-filled silicone foam (Silpak SF-2000) which acoustically and electrically isolates the transducers from each other. FIG. 5 shows that one electrode of each transducer is connected to a common electrical ground 35 and the other electrode of each transducer 10.j is connected to an electrical strip line 42.j which is etched on a printed circuit board 40. Electrical signals are routed to and from each transducer along these strip lines 42.

Electrical Circuit

Figure 6:
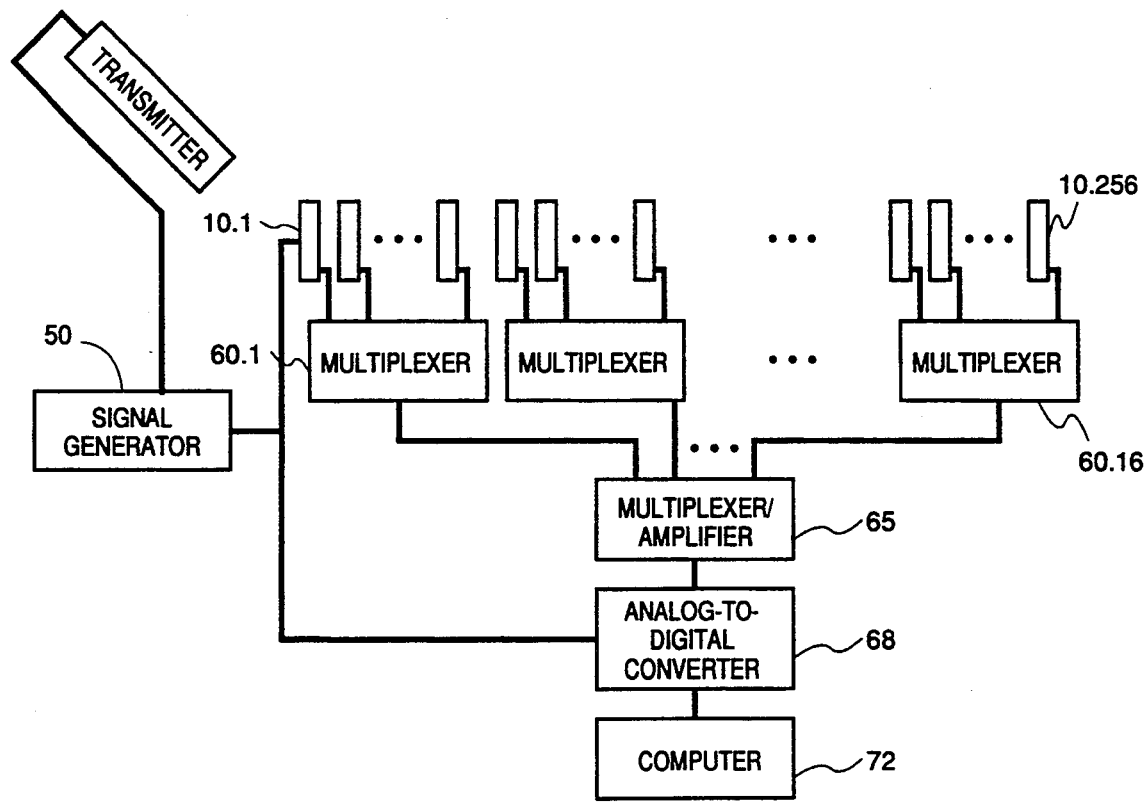
FIG. 6 is block diagram illustrating the electrical circuitry used in the processing of electrical signals from the transducers and the transmission of electrical signals to the transducers.

A block diagram of the electrical processing circuitry is illustrated in FIG. 6. The electrical lines from the 256 transducers 10.j are connected through the electrical strip lines 42 to the inputs of sixteen 16-to-1 analog multiplexers 60.1, ..., 60.16 where they are multiplexed. Each of the 16 output lines of these multiplexers are again multiplexed to a single line via another 16-to-1 analog multiplexer/amplifier 65. The output of this multiplexer 65 is sent to an analog-to-digital converter 68 which is synchronized with the signal from the signal generator 50. The digitized data from the analog-to-digital converter is stored in a computer 72 which for our prototype was a conventional 486 personal computer.

Creating the Image

This invention can produce a two-dimensional map of the magnitude of the scattering potential of a medium moving within tissue which is semi-transparent to acoustic waves. The operation of this invention can be divided into two steps:

1. Collection of scattered wave information in the form of a complex time series.
2. Numerical calculation of the magnitude of the scattering power $S(\vec{r},\omega)$.

The two operational steps are described in detail below.

As described above the raw data collected by the piezoelectric receivers are instantaneous real scalar measurements of pressure at each transducer. In theory, a simple set of time series of the pressure at each receiver 10.j can be used to compute $X_j(\omega)$, defined in equation (2) and the covariance matrices $R_{ij}(\omega)$, equation (6), for any Doppler frequency shift. In practice however, the amount of data, electronics, and computations required to resolve fluid velocities typical in a blood vessel from a set of N distinct time series makes this approach unreasonable. So, a priori knowledge about the narrowband nature of the sonic signal received at the transducers is used to reduce the amount of data required. For blood flow, $|v| \leq 3$ m/s while $c \approx 1500$ m/s, and since the Doppler frequency shift for a fluid traveling with velocity v is $\Delta f = f_o (v/c)\cos\theta$. Therefore we know that the acoustic signal received at the transducers is narrowband with a bandwidth less than $2f_o v/c$. And since $p_j(t) = m_j(t)\exp[i\omega_o t]$ $$\int m_j(t) e^{-i\omega t} dt = \int p_j(t) e^{i\omega_o t} e^{-i\omega t} dt, \quad (25)$$

$$X_j(\omega) = P_j(\omega - \omega_o), \quad (26)$$

where the capital letter signify Fourier transforms. But, as described above, $p_j(t)$ is narrowband and therefore we need only sample $m_j(t)$ at a sample rate sufficient to accurately resolve a bandwidth of at most $2\Delta f$.

The Doppler spectrum $X_j(\omega)$ (j=1, . . . , N) for each transducer is collected by the embodiment in the following fashion. A single frequency sinusoidal electrical signal is sent from the signal generator 50 to the insonifying transducer 11 which transmits this signal as an acoustic wave into the medium 12. The transmitted acoustic wave scatters from the inhomogeneities of medium 12. The sound waves scattered from inhomogeneities which are moving relative to the insonifying transducer are therefore shifted in frequency. The scattered wave from the moving (blood) and stationary (other tissue) inhomogeneities impinge upon the N transducers 10.1, . . . , 10.256 which transform these acoustic signals into narrowband electrical signals. The electrical signals from the receiver transducers are sequentially routed to the analog-to-digital (A/D) converter 68 as shown on FIG. 6. The multiplexers are programmed so that the A/D converter will sample each transducer 10.j four times before the next signal, from the 10.(j+1) transducer, is routed to it. The sample rate of the A/D is set to $$\left( \delta t = \frac{2\pi}{4\omega_o} \right)$$

and the four samples are used to compute $m_j(t)$ for each channel. The result is stored in the computer's memory. This process is then repeated L times so that a time series of $m_{j,l} = m_j(l\Delta T)$ is computed for each transducer, where (l=1,2, . . . , L) and $\Delta T$ is the time elapsed between gathering the four samples required to compute $m_{j,l}$ and the four samples required to compute $m_{j,l+1}$. For N=256 transducers $$\Delta T = T_d + 256(4\delta t + t_d), \quad (27)$$

where $T_d$ is a user selectable delay time which can be varied depending on the magnitude of the anticipated Doppler shift, and $t_d$ is a fixed delay time which allows the electrical signal to settle after the multiplexer switches between channels.

A fast-fourier-transform (FFT) of length L is then computed on the data for each transducer yielding the quantities $X'_j(\omega)$. The quantity $X_j(\omega)$ is formed by multiplying the result of the Fourier transform by a complex value to compensate for the temporal offset between the time series for different receiver channels.

The result may be expressed as $$X_j(\omega) = X'_j e^{i\omega j(4\delta + t_d)} \quad (28)$$

This step is required because the individual transducers are sampled sequentially rather then simultaneously so that each element in the time series for the 10.j transducer is delayed by $j(4\delta t + t_d)$. The covariance matrix $R_{ij}$ is formed for a particular frequency, shift $\omega$ by averaging the product $X_i(\omega)X_j^*(107)$ for several sets of measurements—for the tests conducted with the prototype system 40–50 sets of measurements were averaged when generating the coefficients of $R_{ij}$. Finally, the two-dimensional image of $S(\bar{r},\omega)$ is then generated using one of the reconstruction algorithms discussed previously.

Software

Figure 7:
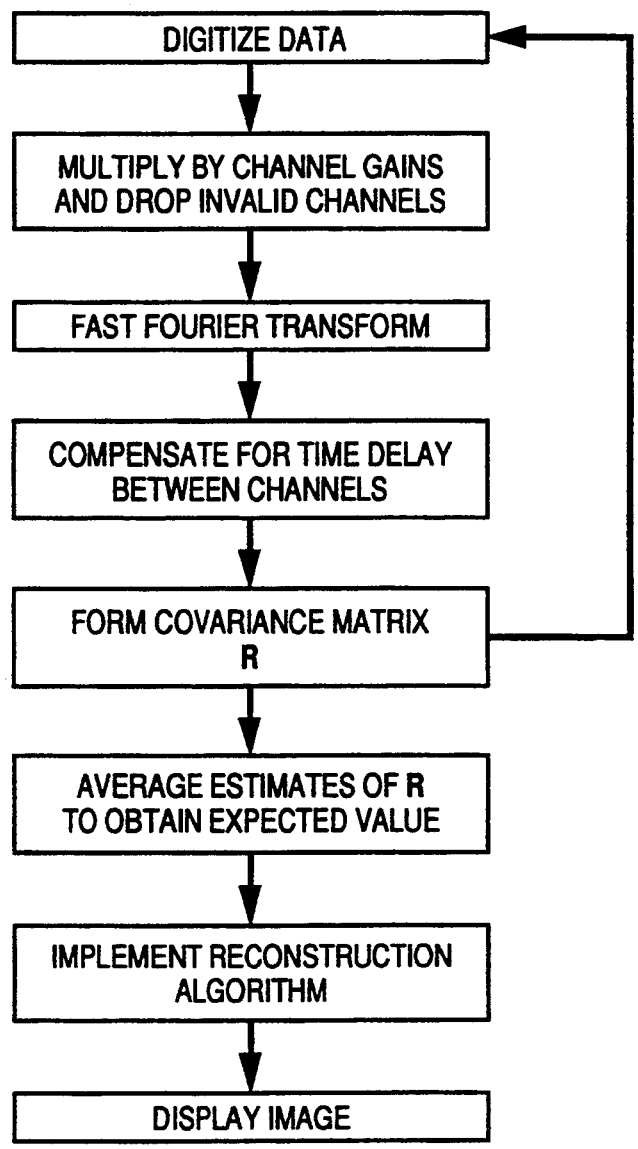
FIG. 7 is a block diagram showing the principal steps utilized in creating a Doppler image using a preferred embodiment of the present invention.

Our computer software can be described by FIG. 7 which outlines the steps required to process the wave data for the image.
  Step 1: Normalizes receiver data.
  Step 2: Fast-Fourier-transforms $m_{j,l}$
  Step 3: Compensates for time delays between channels.
  Step 4: Computes $R_{ij}$ from several sets of measurements.
  Step 5: Reconstructs 2-dimensional image from $R_{ij}$.

Computer Simulation

A computer simulation of the system was developed to test the reconstruction technique. This simulation uses an assumed antenna pattern $D_j$ (monopole, dipole or higher order function) to compute the signal at each receiver 10.j from a set or scattering points in the medium. Random noise commensurate to the noise expected in the real system is added to each measurement $X_j(\omega)$. Each scattering point is assigned a fixed magnitude scattering power $S(\bar{r},\omega)$, and imparts a random phase shift to the scattered wave. Simulated measurements from several realizations of the random phase shift associated with $S(\bar{r},\omega)$ are used to form the covariance matrix $R_{ij}$ for a given Doppler shift. The reconstruction algorithms compute the scattering power $S(\bar{r},\omega)$ which is then compared to the known power distribution.

Figure 8:
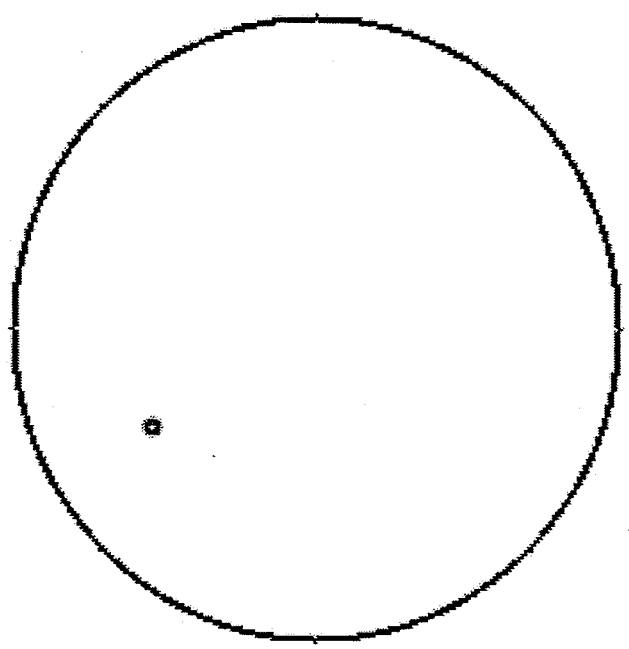
FIG. 8 is a simulated computer reconstructed image of flow in a cylindrical vessel using the mathematical processes according to the present invention. The simulation utilizes 128 transducers arranged regularly on a 120° circular arc.
Figure 9:
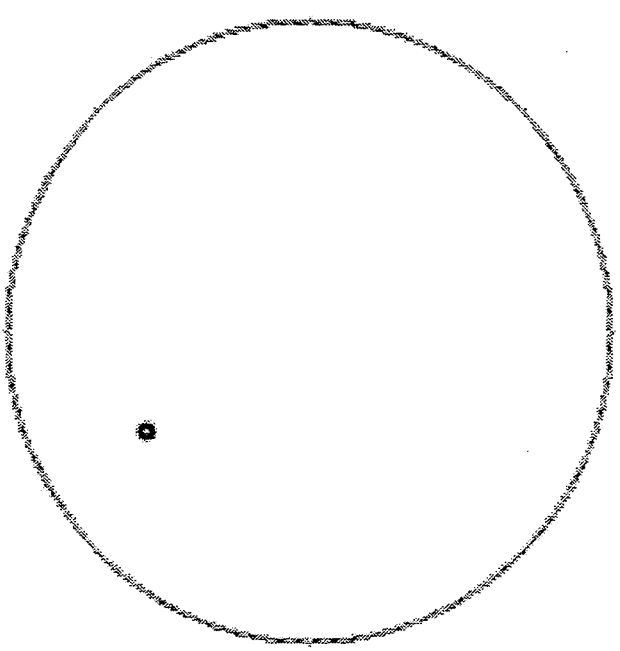
FIG. 9 is a simulated computer reconstructed image of flow in a cylindrical vessel using the mathematical processes according to the present invention. The simulation utilizes 64 transducers spaced regularly on a 120° circular arc.

The results of the simulation are shown in FIGS. 8 and 9. FIG. 8 shows a reconstruction at a single velocity of simulated blood flow in a cylindrical vessel. A 120° circular receiver arc is simulated with N=256. The flow field is assumed to be fully developed and laminar, with a velocity profile described by $$V = v_o \left( 1 - \left( \frac{a}{a_o} \right)^2 \right),$$

where $v_o$ is the maximum velocity of the blood at the center of the vessel, $a_o$ is the radius of the vessel, and a is the radial dimension measured from the center of the vessel. The image is an annulus corresponding to fluid with uniform velocity at a radius $a = \lambda_o$. FIG. 9 shows the same image reconstructed using only 64 receiver transducers arranged at uniform intervals in an arc of 120°.

Actual Images

Figure 10:
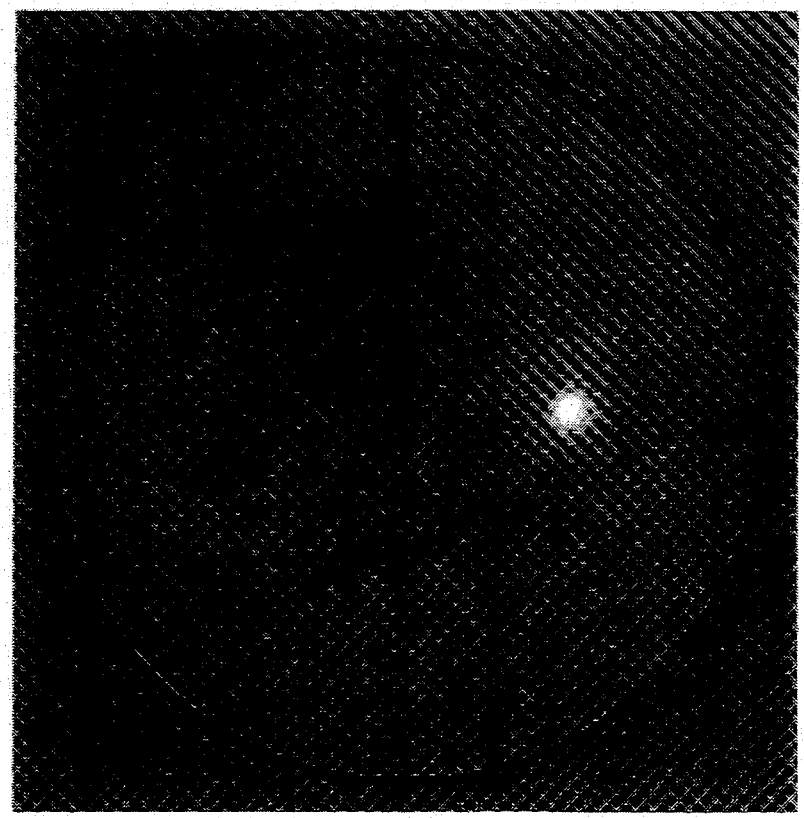
FIG. 10 is a computer reconstructed image using actual flow data. Image consists of flow through two tubes with 5 mm inner diameters and with equal but opposite flow velocities.
Figure 11:
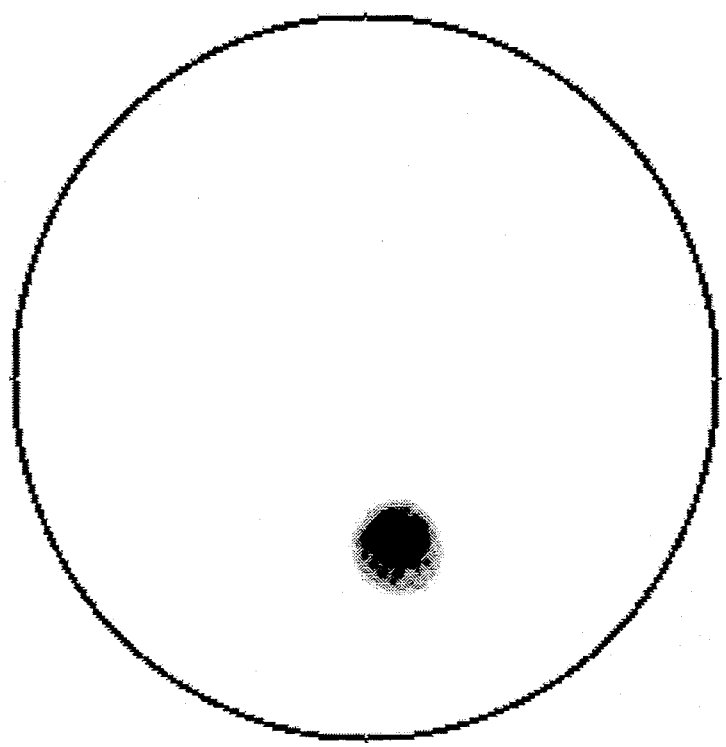
FIG. 11 is a computer reconstructed image using actual flow data. Image consists of flow through a single tube with 15 mm inner diameter.

FIGS. 10 and 11 show actual images obtained using the prototype device described above by reference to FIG. 3. The data was obtained with a full receiver ring of 256 receiver transducers 10. The transducer ring was mounted on a water reservoir such that the z axis (the normal to the image plane) was vertical. The reservoir was filled so that the transducer elements were submerged. The insonifying transducer 14 was placed above the receiver ring and was also submerged in the water bath.

FIG. 10 is a reconstruction of flow within the latex tube of inner diameter 0.5 cm shown in FIG. 3. The axes of the tubes 15 were perpendicular to the image plane and the flow within the tubes was equal in magnitude but opposite in direction: one flowing downward through the plane the other upwards through the imaging plane. Since the sound waves scattered by the fluid in the different tubes have different Doppler shifts, the two Doppler frequency bands were reconstructed separately to form the entire image. First the covariance matrix corresponding to a positive Doppler shift, $R_{ij}(\omega)=X_i(\omega)X_j^*(\omega)$, was used to reconstruct the image of the flow within the tube carrying the liquid upwards out of the reservoir. Next the data corresponding to a negative Doppler shift $R_{ij}(-\omega)$ was used to reconstruct the flow within the other tube. To form the final image the two reconstructions were combined and the results are indicated on monitor 19 in FIG. 3. FIG. 10 is the actual computer generated image. Flow differences in color are shown on monitor 19.

FIG. 11 is a reconstruction of a single latex tube with diameter 1.5 cm. The flow within this tube is downwards into the reservoir.

Three-Dimensional Imaging

Three-dimensional images of moving fluid can be obtained by reconstructing $S(\bar{r},\omega)$ as two-dimensional cross-sectional slices juxtapositioned in the z-direction and then stacking these slices to tom the three-dimensional image. The acoustic signal data used to reconstruct the two-dimensional slice images can be collected using a single one-dimensional array of transducers which is mechanically moved in the z-direction.

Alternatively, the acoustic signal data can be collected by using rows of one-dimensional transducer arrays arranged in the z-direction (i.e. a two-dimensional array). Again, acoustic data from each row of one-dimensional arrays is used to reconstruct $S(\bar{r},\omega)$ as separate two-dimensional cross-sectional images and then these images are stacked to form a three-dimensional image. Beam forming in the z-direction (i.e. phase weighted summing of individual transducer array elements spaced in the z-direction) can be used to reduce the slice thickness and increase resolution in the z-direction.

Finally, acoustic signal data can be collected with the entire two-dimensional array and this entire data set can be used to reconstruct $S(\bar{r},\omega)$ directly as a three-dimensional image.

Alternate Embodiments

Alternate embodiments of the invention also include the geometry of the transducer array. These alternate embodiments may be appropriate to facilitate coupling of the acoustic waves to various blood vessels in different parts of the human body including, for example, arteries and veins in the legs, arms, and neck.

Figure 4B:
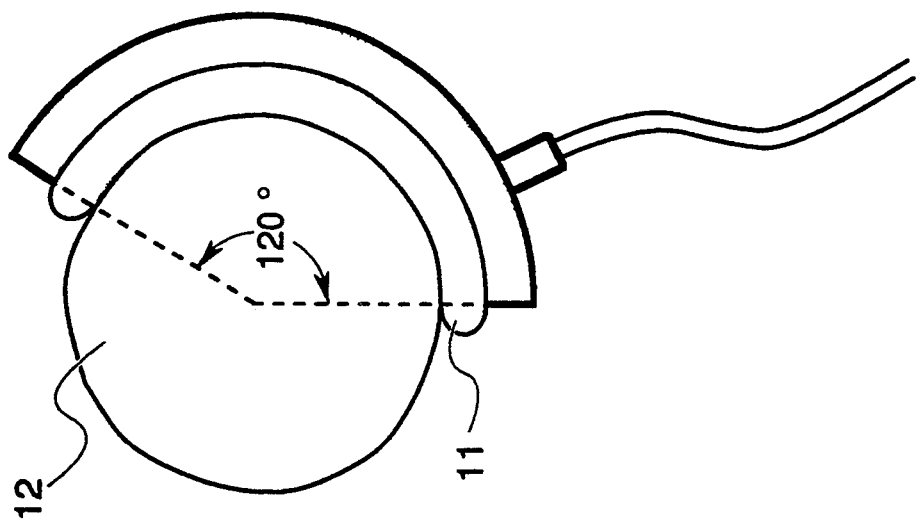
FIG. 4 is a schematic diagram of the invention used to image blood flow in a leg.
Figure 4A:
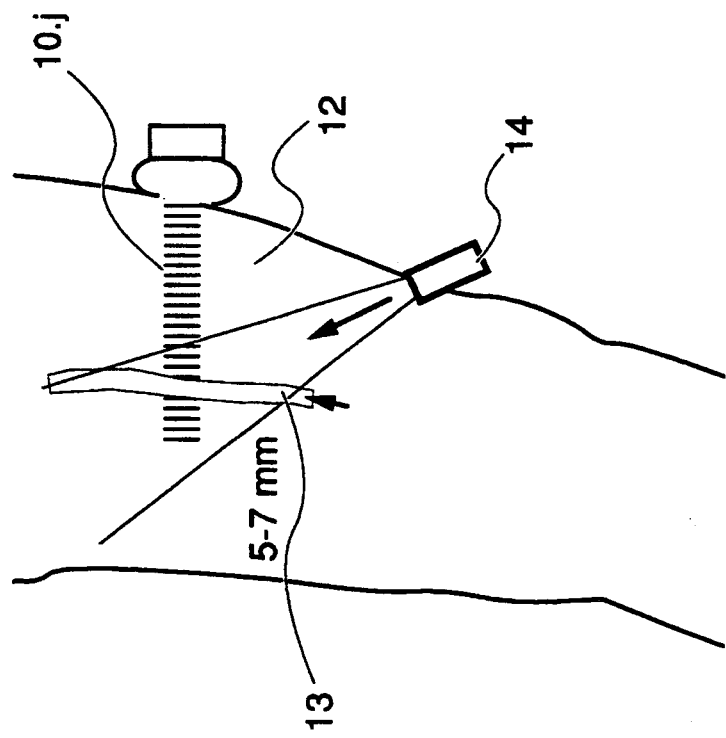

The number and arrangement of the receiver transducers may be changed to fit the purpose of the device. The receiver array may be fabricated in either a circular ring as described above or a circular arc. Preferred design would provide arcs of at least 60°. The number of receiver transducers may be varied from as few as 8 to more than 3072. The arrangement of transducers on the ring may be at regular intervals or random intervals. Designs which are not circular may be used, but the algorithms for reconstructing the image will be more complicated. FIGS. 4A and 4B depict an embodiment of the present invention using transducers arranged in a 120° arc. This embodiment uses a fluid-filled bladder instead of a water bath to couple the acoustic signals into and out of the tissue. Persons skilled in the art of imaging devices can derive such modified algorithms using the principles described above.

An alternate embodiment concerns the vertical (z coordinate) dimension of the receiver transducers. The vertical dimension may be made smaller to image a narrower slice of the body or larger to average a larger slice.

An alternate embodiment concerns the nature of the insonifying transducer. The beam pattern emanating from this transducer may be broad to illuminate all the tissue inside the arc, or may be very narrow so that the operator may chose to look at only a select portion of the tissue. Another preferred embodiment would utilize a phased array of transducers so as to direct the insonifying beam to particular locations in the tissue.

An alternate embodiment concerns transmitting waves containing, multiple frequency components and using the added information to enhance the reconstructed images. Time-gating the reception of the multiple frequencyt pulses allows further discrimination of flowing fluid versus static tissue signals thus increasing the signal-to-noise ratio of the device. The reader should construe the above described embodiments of this invention as examples, and the scope of this invention shall be determined by the appended claims and their legal equivalents.

What is claimed is:

1. A Doppler imaging device for providing images of a fluid, containing randomly located scatterers, flowing through a medium comprising:
   a) an acoustic transmitting means for transmitting acoustic waves into said medium,
   b) an array of at least eight acoustic signal detection means, each detection means defining a channel, for detecting at a plurality of locations acoustic signals reflected from said medium including signals reflected from said scatterers moving in said medium,
   c) a computer means for computing images of said fluid moving in said medium utilizing said reflected signals said computer means comprising:
      i) conversion means for converting said reflected acoustic signals for each channel into frequency information in order to determine the amplitude of said reflected acoustic signals at at least one Doppler shifted frequency,
      ii) a correlation means for forming time averaged detection means channel-to-channel amplitude correlations, iii) an image formation means for forming images of said fluid moving in said medium using said amplitude correlations.

2. An imaging device as in claim 1 wherein the said scatterers are blood cells in blood moving through tissue.

3. An imaging device as in claim 1 wherein said correlation means comprises a means for calculating a covariance matrix using said amplitude determinations.

4. An imaging device as in claim 3 wherein each of said at least eight signal detection means defines an antenna pattern described in vector form and said image formation means further comprises a matrix manipulation means for calculating said images by a mathematical manipulation of said covariances matrix and said antenna patterns.

5. An imaging device as in claim 4 wherein said at least eight signal detection means define K signal detection means as 1, 2 . . . i, j, . . . K signal detection means and said matrix manipulation means utilizes an algorithm substantially equivalent to the following algorithm:

$$R_{ij}(\Delta\omega_n) = \frac{1}{K} \sum_{R=1}^{K} X_i^{(R)}(\Delta\omega_n) X_j^{*(R)}(\Delta\omega_n)$$

where:
$X_i^{(R)}(\Delta\omega_n)$ represents acoustic signal information at i detection means corresponding to said at least one Doppler shifted frequency band, $\Delta\omega_n$.
$S_j^{*(R)}$ is the complex conjugate of an approximation of $X_j^{(R)}(\Delta\omega)$.
$R_{ij}(\Delta\omega_n)$ is covariance matrix of K independent realizations of $X_i^{(R)}(\Delta\omega_n)$.

6. An acoustic imaging device as in claim 4 wherein said mathematical manipulation of said covariance matrix comprises an aberration correction means for correcting said antenna patterns for aberration.

7. An acoustic imaging device as in claim 1 wherein said locations of said detection means are along a single plane at least partially surrounding said medium, said plane defining a first image plane.

8. An acoustic device as in claim 7 for obtaining three-dimensional images, said device further comprising a vertical adjustment means for moving said array of detection means in a direction perpendicular to said image plane in order to obtain a plurality of parallel images.

9. An acoustic device as in claim 6 for obtaining three-dimensional images, said device further comprising a vertical adjustment means for moving said array of detection means in a direction perpendicular to said image plane in order to obtain three dimensional images.

10. An acoustic imaging device as in claim 7 wherein the said locations of said detection means are arranged at regular intervals on an arc.

11. An acoustic imaging device as in claim 7 wherein the locations of said detection means are ganged at irregular intervals on an arc.

12. An acoustic imaging device as in claim 7 wherein the locations of said detection means are arranged at regular intervals on one or more planar array segments.

13. An acoustic imaging device as in claim 7 wherein the locations of said detection means are arranged at irregular intervals on one or more planar array segments.

14. An acoustic imaging device as in claim 1 wherein said locations of said detection means are along a plurality of parallel planes at least partially surrounding said medium, each of said planes defining an image plane, said plurality of planes defining a vertical direction perpendicular to said planes.

15. An acoustic imaging device as in claim 14 for obtaining three-dimensional images, wherein said image formation means is a means for forming three-dimensional images by stacking two-dimensional images.

16. An acoustic imaging device as in claim 14 for obtaining three-dimensional images, wherein said image formation means is a means for forming said three-dimensional images using said amplitude correlations.

17. An acoustic imaging device as in claim 16 for forming three-dimensional images wherein said beamforming means is programmed to provide information for computing said three-dimensional images.

18. An acoustic imaging device as in claim 14 wherein each of said detection means defines an individual antenna pattern for that detection means and further comprising a beam forming means for forming beam patterns comprising weighted sums of individual detection means.

19. An acoustic imaging device as in claim 1 wherein said transmitting means is adapted to transmit acoustic waves at at least one narrow band frequency.

20. An acoustic imaging device as in claim 1 wherein the broadcasting means comprises a multi frequency broadcasting means for broadcasting a plurality of narrow band frequencies.

21. An acoustic imaging device as in claim 1 wherein said transmitting means is adapted to transmit pulses of acoustic waves.

22. An acoustic imaging device as in claim 1 wherein the detection means are transducers constructed from piezoelectric zirconate titanate.

23. An acoustic imaging device as in claim 1 wherein the detection means are transducers constructed from a piezoelectric film.

24. An acoustic imaging device as in claim 1 wherein the detection means are transducers constructed from a piezoelectric composite.

25. An acoustic imaging device as in claim 1 further comprising a water bath means for coupling said detection means to said medium.

26. An imaging device as in claim 1 wherein said acoustic transmitting means comprises a phased array of transducers.

27. An imaging device as in claim 26 wherein said phased array of transducers broadcast signals to a plurality of different locations in said medium and said image generation means comprises a sequential process means for creating said image by combining a plurality of images.

28. A process for generating an image of a fluid, containing randomly located scatterers, moving through a medium utilizing
   a) at least 8 acoustic signal detection means, each signal detection means defining a channel,
   b) an acoustic broadcasting means for broadcasting into said medium an acoustic signal, and
   c) a data acquisition, digitalization and accumulation means;
comprising the steps of:
   i) broadcasting into said medium an acoustic signal,
   ii) accumulating in digital form, a series of pressure signals representing acoustic waves reflected from said medium including acoustic waves reflected from said moving scatterers so as to define a set of pressure data in a time domain.

iii) convening said set of pressure data in said time domain into a set of pressure signal information in a frequency domain, said frequency domain comprising at least one frequency corresponding to a Doppler shifted frequency created by the reflection a portion of said acoustic signal from Said moving scatterers, iv) forming channel-to-channel amplitude correlations using said pressure signal information at said at least one frequency corresponding to said Doppler shifted frequency, and v) generating an image of said fluid moving within said medium from said amplitude correlation.

29. A process as in claim 28 wherein each signal detection means defines an antenna pattern and such antenna patterns are utilized in conjunction with said amplitude correlations to form said image.

* * * * *